United States Patent [19]

Priegnitz et al.

[11] Patent Number: 5,518,625
[45] Date of Patent: May 21, 1996

[54] CHIRAL SEPARATIONS BY SIMULATED MOVING BED CHROMATOGRAPHY OPERATING AT LOW K' VALUES

[75] Inventors: James W. Priegnitz, Elgin; Beth McCulloch, Clarendon Hills, both of Ill.

[73] Assignee: UOP, Des Plaines, Ill.

[21] Appl. No.: 387,984

[22] Filed: Feb. 13, 1995

[51] Int. Cl.⁶ ............................................. B01D 15/08
[52] U.S. Cl. ................................. 210/659; 210/198.2
[58] Field of Search .......................... 210/635, 656, 210/659, 198.2; 435/280

[56] References Cited

U.S. PATENT DOCUMENTS

| | | | |
|---|---|---|---|
| 5,126,055 | 6/1992 | Yamashita | 210/659 |
| 5,407,580 | 4/1995 | Hester | 210/635 |
| 5,433,793 | 7/1995 | Herber | 127/46.1 |
| 5,434,298 | 7/1995 | Negawa | 210/659 |
| 5,434,299 | 7/1995 | Negawa | 560/248 |

*Primary Examiner*—Ernest G. Therkorn
*Attorney, Agent, or Firm*—Thomas K. McBride; Eugene I. Snyder

[57] ABSTRACT

Resolution of a racemic mixture of organic materials by simulated moving bed chromatography using a chiral stationary phase can be routinely effected at atypically low values of k' with recoveries of at least 95% and an optical purity of at least 95%. In particular, values in the range $0.1 < k' < 1.0$ are recommended with a resulting savings in mobile phase consumption, inventory, and recovery.

3 Claims, 6 Drawing Sheets

CHIRAL SEPARATIONS BY SIMULATED MOVING BED CHROMATOGRAPHY OPERATING AT LOW K' VALUES

BACKGROUND OF THE INVENTION

This application deals with the use of chromatography in commercial scale preparative separations. More particularly, our invention deals with the branch of simulated moving bed chromatography as applied to the separation of chiral substances from a racemic mixture. Our contribution to such separations which is the subject of this application arises from the recognition that operating at low values of k', the capacity factor, is quite beneficial in chiral separations even though classical liquid chromatography theory teaches operation at high values of k' as one prerequisite to successful separations. To better understand our invention in the context of theory and conventional practice it will be helpful to briefly review some of the relevant principles of liquid chromatography.

One fundamental property in liquid chromatography is k', the capacity factor, which is defined as $$k' = \frac{n_s}{n_m} \quad (1)$$

where $n_s$ is the total moles of material being separated in the stationary phase and $n_m$ is the number of moles in the mobile phase. Where there are several components present, the capacity factor for the ith component is $$k'(i) = \frac{n_s(i)}{n_m(i)}$$

The retention time, $t_r$, for component i, $t_r(i)$, is related to the time it takes for the mobile phase to travel the length of the column, $t_0$, by the distribution of component between the stationary and mobile phases according to the equation, $$t_r(i) = \frac{t_0}{\left[\frac{n_m(i)}{n_m(i)+n_s(i)}\right]} = t_0 \frac{[n_m(i)+n_s(i)]}{n_m(i)} \quad (2)$$

$$t_r(i) = t_0[1+k'(i)]$$

Rearranging, $$k'(i) = \frac{t_r(i)-t_0(i)}{t_0(i)}$$

Thus, the capacity factor k' also is related to the relative retention time of the component in question.

For two components, the ratio of their relative retention times, α, is $$\alpha_{ij} = \frac{t_r(i)-t_0}{t_r(j)-t_0} = \frac{k'(i)}{k'(j)}$$

where $\alpha_{ij}$ is the selectivity factor between components i and j. Finally, the volume, $V_r$, of the mobile phase required to elute a component as measured to the apex of the peak is related to the flow rate, F, of the mobile phase and retention time of the component by, $$V_r(i) = t_r(i)F$$

from which it follows that $$V_r(i) = V_0[1+k'(i)] \quad (4)$$

$$[V_r(i)-V_0]/V_0 = k' \quad (5)$$

and $$\frac{V_r(i)-V_0}{V_r(j)-V_0} = \frac{t_r(i)-t_0}{t_r(j)-t_0} = \frac{k'(i)}{k'(j)} = \alpha_{ij} \quad (6)$$

Thus, classical liquid chromatography theory as supported by much experimental evidence leads to the conclusions that the retention volume of a particular component, relative to the retention volume of the pure mobile phase, depends only on the capacity factor for the component, although relative retention volumes and relative retention times for two components depend only on the ratio of the two capacity factors, and it is the ratio of the capacity factors which define selectivity.

One form of chromatography well adapted to continuous, commercial-size separation is simulated moving bed chromatography. In continuous moving bed chromatography the stationary phase moves relative to the feed and mobile phase inputs, and the extract and raffinate outputs. Because of the difficulty of implementing a moving stationary phase in chromatographic separations its simulation is favored in practice (hence the name simulated moving bed chromatography) where incremental positional changes of the input and output streams, relative to a static stationary phase, is effected at regular intervals. Although many of the foregoing relations apply to simulated moving bed chromatography some additional nuances are applicable when the separations are of chiral substances using conventional chiral stationary phases.

One important observation from the foregoing review of some salient theoretical aspects of liquid chromatography is the affect of k' on the retention time and retention volume, $$k' = t_r - t_0 = V_r - V_0$$

Whereas one normally seeks to maximize the difference in retention time between a component and the mobile phase in order to increase the difference in retention time between two components, this requires a large k' which has the ancillary undesirable effect of increasing the retention volume of the mobile phase for the components. Thus, the accepted practice in analytical chromatography and in batch mode preparative chromatography of operating at a high k', usually in the range 1<k'<10, has as a necessary consequence the usage of a large volume of mobile phase.

We have found the conditions in simulated moving bed chromatography can be significantly modified from those required for analytical and batch mode preparative chromatography. In particular, the separation of enantiomers from their racemic mixture using a chiral stationary phase in simulated moving bed chromatography can be performed effectively at low values of k', thereby minimizing the amount of mobile phase which is needed. Specifically, chiral separations may be performed efficiently where k' is less than 1, and especially in the range 0.1<k'<1. Since an appreciable cost of the separation process is associated with the mobile phase and its recovery from the raffinate and extract streams, our process affords substantial cost savings accruing from a lower mobile phase inventory, lower utility costs in recovering the mobile phase, and other ancillary costs.

It needs to be mentioned that even though certain types of separation currently effected by simulated moving bed (SMB) processes operate at the equivalent of a low k' it is not obvious to extend this knowledge to chiral separations because the mechanism of adsorption is fundamentally different. Thus, the adsorbents used in traditional separations such as that of the xylene isomers are zeolites such as X faujasites that have a high ion exchange capacity. With zeolites, the primary mechanism for adsorption is electrostatic attraction. The heat of adsorption, which is a direct measure of strength of the bonding between the adsorbate and the surface, is high (typically ca. 20 kcal). Consequently, a "strong" desorbent is required in these systems. Frequently, the desorbent is similar in polarity to that of the feed component. For example, xylenes are desorbed with alkyl aromatics a=such as p-diethylbenzene or toluene and chlorinated aromatic feedstocks are typical desorbed with chlorinated aromatic solvents. The strong adsorbate/adsorbent interaction and the high binding energies require the use of a strong desorbent.

The stationary phases used in chiral separations consist of an organic moiety bonded to an underlying inert core support such as silica. The mechanism of adsorption is very different from that of zeolites in that weak van der Waals forces predominate. Frequently, the adsorbate partitions in the "liquid phase" which is defined by the organic coating and molecules of the mobile phase. The binding energies are less than 1 kcal and the mobile phases are typically weak. Consequently, manipulation of the mobile phase composition and the use of "strong mobile phases" is unexpected for the very weak intermolecular interactions encountered with racemic organic molecules which are the feedstocks separated according to this invention. We also shall see that solubility plays a more significant role in our invention than in prior SMB separations.

SUMMARY OF THE INVENTION

The purpose of this invention is to separate at least one enantiomer from a chiral organic material by simulated moving bed chromatography using a stationary phase having chiral recognition sites and an achiral liquid mobile phase by operating under separation conditions characterized by a low capacity factor for at least one of the separated enantiomer(s). In an embodiment $0.1<k'<1.0$. In a more specific embodiment $0.3<k'<1.0$.

DESCRIPTION OF THE INVENTION

Figure 1:
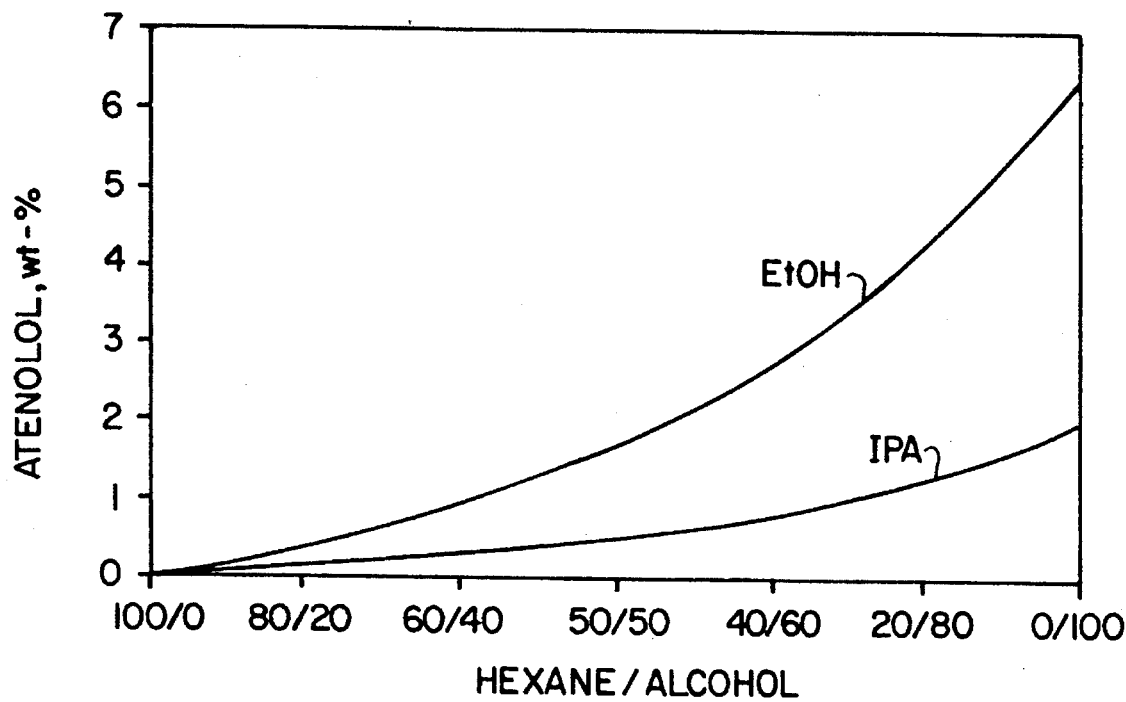
FIG. 1 portrays the solubility properties of racemic atenolol in a hexane-isopropyl alcohol mixture.

Our invention results from the recognition that although a high value of retention capacity (i.e., capacity factor), $k'$, is desirable and is usually posited as a necessary condition for the successful separation of two materials in traditional liquid chromatography, such a requirement is neither necessary nor desirable in effecting the successful separation of enantiomers of chiral materials by simulated moving bed chromatography. Because the volume of the mobile phase used in eluting a material is proportional to $k'$, a consequence of high $k'$ values is a relatively large usage of the mobile phase. The larger the mobile phase usage, the higher the cost due to an increased solvent inventory, increased cost of recovering the separated component from a larger volume of mobile phase, and higher inadvertent losses of mobile phase. Employing our invention leads to a substantial cost reduction and operating efficiency in separating enantiomers of chiral materials. In particular, our invention relates to the use of simulated moving bed chromatography for the separation of at least one enantiomer from a mixture of chiral organic materials using an achiral mobile phase and a solid stationary phase having at least one chiral recognition site in one or more organic materials. The core of our invention is operating the SMB process under conditions where at least one of the enantiomers has a low retention capacity, specifically $0.1<k'<1.0$ In traditional liquid chromatography $1.0<k'<10$. This condition has been used as both a desirable and necessary condition for adequate separation of components of interest. In simulated moving bed chromatography as applied to the separation of enantiomers of chiral organic materials using a stationary phase having chiral recognition sites and an achiral mobile phase, we have found adequate separation can be achieved at $0.1<k'<1.0$. The benefits which flow need not be repeated; vide supra.

EXAMPLES

The methodology used to identify the conditions for simulated moving bed (SMB) operation is discussed and exemplified. The optimal conditions can be readily identified by analyzing elution profiles obtained from HPLC (high performance liquid chromatography). Important parameters for optimization are loadability of the support, selectivity, mobile phase strength, and feed solubility. Optimization of these parameters helps identify conditions suitable for a cost-effective separation.

The experimental approach is outlined below. Although we believe our general approach is effective and efficient, we do not mean to imply that other alternatives are unavailable. We make our choice based on convenience, efficacy, and experience.

1. Identify a suitable stationary phase.
2. Determine the solubility properties of the feed material.
3. Identify a mobile phase that gives the best combination of selectivity and solubility.
4. Evaluate the effect of different mobile phase compositions.
5. Select the optimal mobile phase composition subject to the parameters of feed solubility, selectivity, and mobile phase strength.

The following case studies are presented to demonstrate how our experimental approach is applied and to illustrate different scenarios that may be encountered. In the first case the selectivity is high, but the solubility of the feed material is low. In the second case the selectivity is low but the solubility of the feed is high. In the third case, the selectivity varies with mobile phase composition. In each example productivity and mobile phase consumption are calculated from elution profile data for various mobile phase compositions. Optimal SMB conditions are derived from the productivity and mobile phase consumption data.

Definitions

Productivity refers to the amount of feed (in grams) processed per liter of stationary phase per hour.

Mobile phase consumption refers to the amount of solvent required to process one gram of feed.

Target performance in the SMB operation is 99.5% purity of the extracted component and 99% recovery, where recovery refers to the yield of the extracted component.

Separation of Atenolol

The (S) enantiomer of the beta blocker atenolol has fewer side effects than the racemic mixture, hence there is considerable incentive to selectively utilize (S)-atenolol in pharmaceutical preparations.

Stationary phase selection: CHIRALCEL OD, a chiral stationary phase from Daicel, shows good selectivity for (S)-atenolol.

Solubility properties of atenolol. Atenolol has a higher solubility in ethanol than in isopropyl alcohol (IPA) (FIG. 1). The solubility of atenolol is low when a small amount of isopropyl alcohol is present in the hexane-alcohol mixture.

Figure 2:
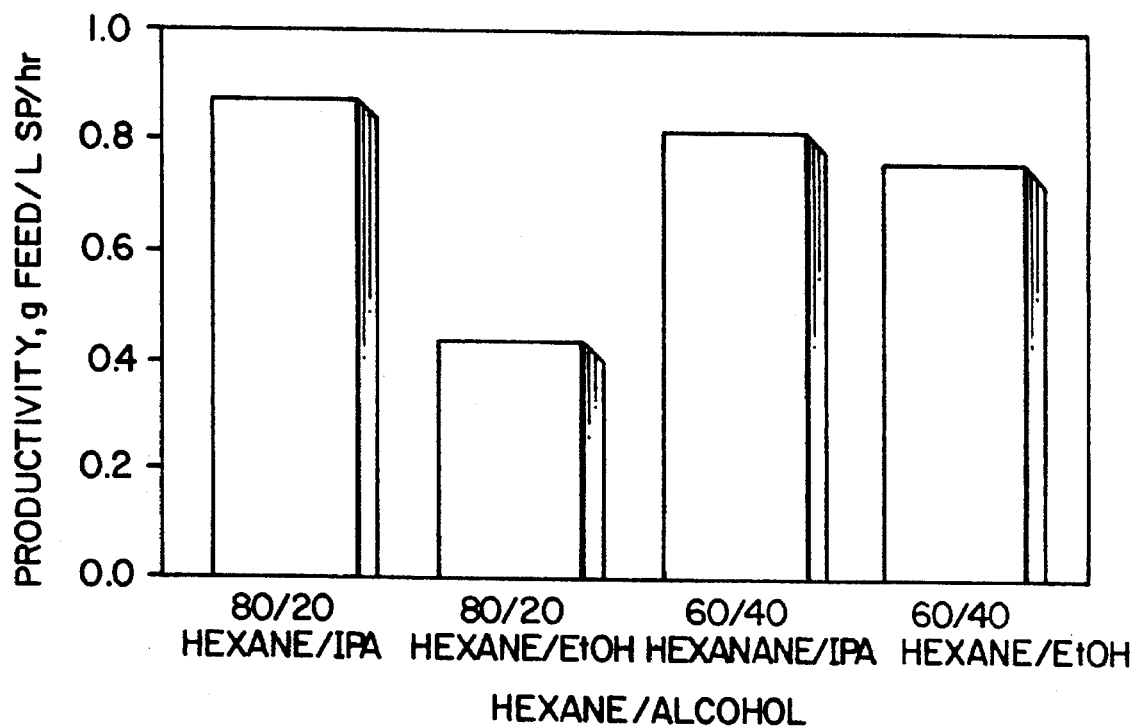
FIG. 2 depicts the productivity for resolution of racemic atenolol with different mobile phases.

Mobile phase selection: A higher alpha (selectivity) is obtained with isopropyl alcohol, but a lower k' (capacity factor) is observed with ethanol (Table 1). Productivity is calculated from the elution profile data by assuming the maximum solubility of atenolol at each mobile phase composition (FIG. 2). The high productivity obtained with the use of isopropyl alcohol indicates that a mixture of hexane and isopropyl alcohol is the preferred mobile phase. The results summarized in Table 1 were obtained using a column of stationary phase 25 cm long with a 0.46 cm inside diameter, the indicated mobile phase also containing 0.1% diethylamine, and a mobile phase flow rate of 1 mL/minute. Analyses were performed at 254 nm.

TABLE 1

Effect of mobile phase on Separation of Atenolol

| Composition, vol-% | | | | |
|---|---|---|---|---|
| Hexane | Alcohol | k'(R) | k'(S) | Alpha |
| 80 | 20 IPA | 4.15 | 7.35 | 1.77 |
| 80 | 20 EtOH | 2.37 | 3.20 | 1.35 |
| 60 | 40 IPA | 0.93 | 1.76 | 1.89 |
| 60 | 40 EtOH | 0.56 | 0.82 | 1.45 |

Figure 3:
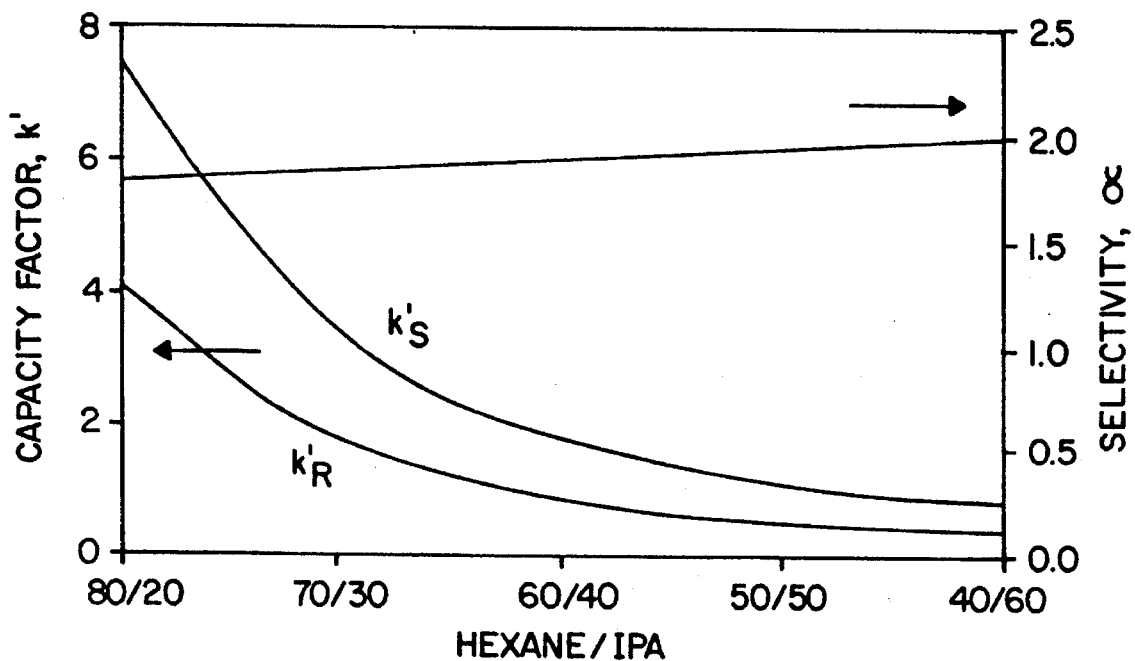
FIG. 3 shows the effect of mobile phase composition on separation of racemic 3-chloro- 1-phenyl-1-propanol.

Effect of mobile phase composition: When the isopropyl alcohol content is increased, the capacity factors are reduced (FIG. 3). The selectivity remains fairly constant.

Figure 4:
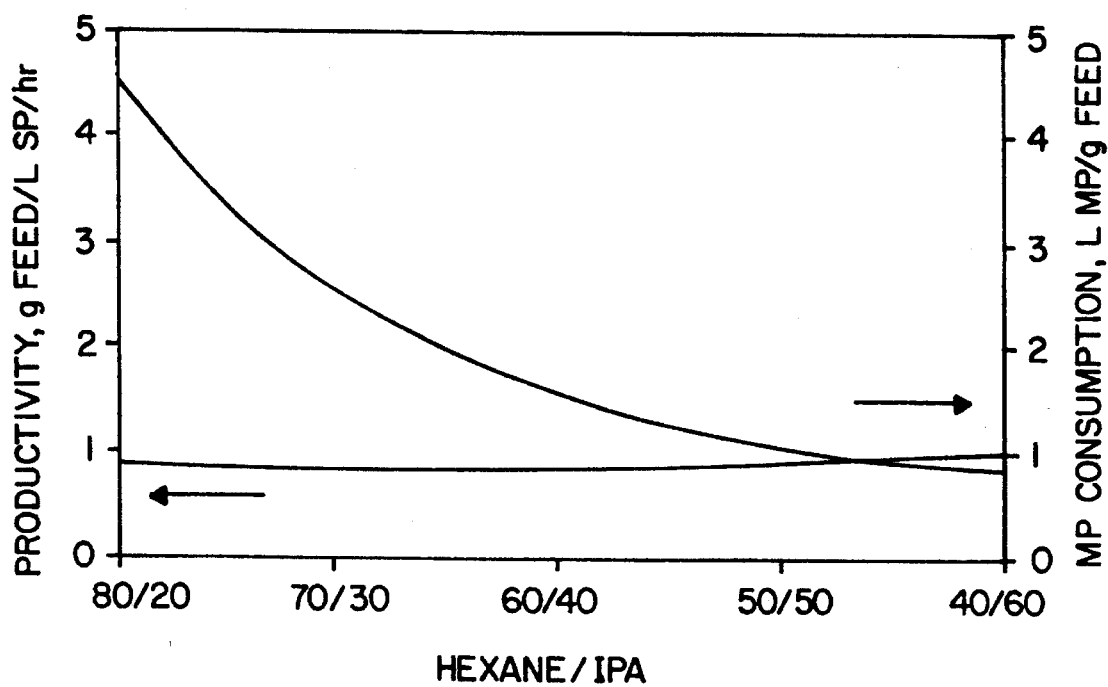
FIG. 4 portrays productivity and solvent consumption as a function of mobile phase composition, assuming maximum solubility, of racemic atenolol.
Figure 5:
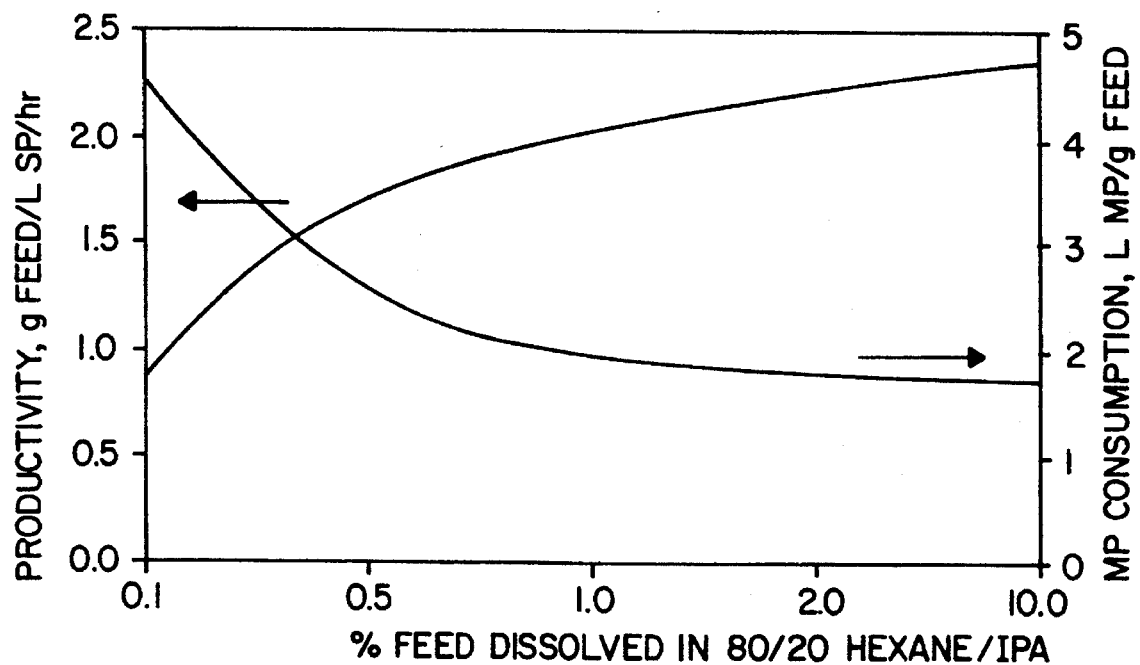
FIG. 5 shows productivity and mobile phase consumption for an 80:20 mixture of hexane:IPA.

Selection of mobile phase composition: Productivity and solvent consumption were determined for each mobile phase composition by assuming the maximum solubility of atenolol at each mobile phase composition (FIG. 4). The stationary phase productivity increases slightly from 0.9 to 1.0 g feed/L stationary phase/hr as the isopropyl alcohol content of the mobile phase is increased. The low productivity is attributed to the low solubility of atenolol in the mobile phase. Productivity increases substantially if the concentration of atenolol in the feed could be increased (FIG. 5). The hypothetical data are shown for the mobile phase composition of a 80-20 mixture of hexane and isopropyl alcohol.

The stationary phase costs are sensitive to the feed concentration. If a 10 weight percent atenolol feed concentration were feasible, the cost of the stationary phase would be reduced by 62% relative to the cost of the stationary phase required to produce 1 kg of S-atenolol where the atenolol feed concentration is 0.1 weight percent.

Conclusions: The solubility of atenolol in a hexane-isopropyl alcohol mixture using CHIRALCEL OD is too low for a cost-effective separation using SMB technology. The low productivity gives rise to a high stationary phase requirement. If atenolol were more soluble, the stationary phase costs could be significantly reduced.

Separation of 3-Chloro-1-Phenyl-1-Propanol

3-Chloro-1-phenyl-1-propanol (CPP) is a chiral intermediate that can be used in the synthesis of a number of antidepressant drugs.

Stationary phase selection: Although CHIRALCEL OD separates the CPP enantiomers, the selectivity is low.

Figure 6:
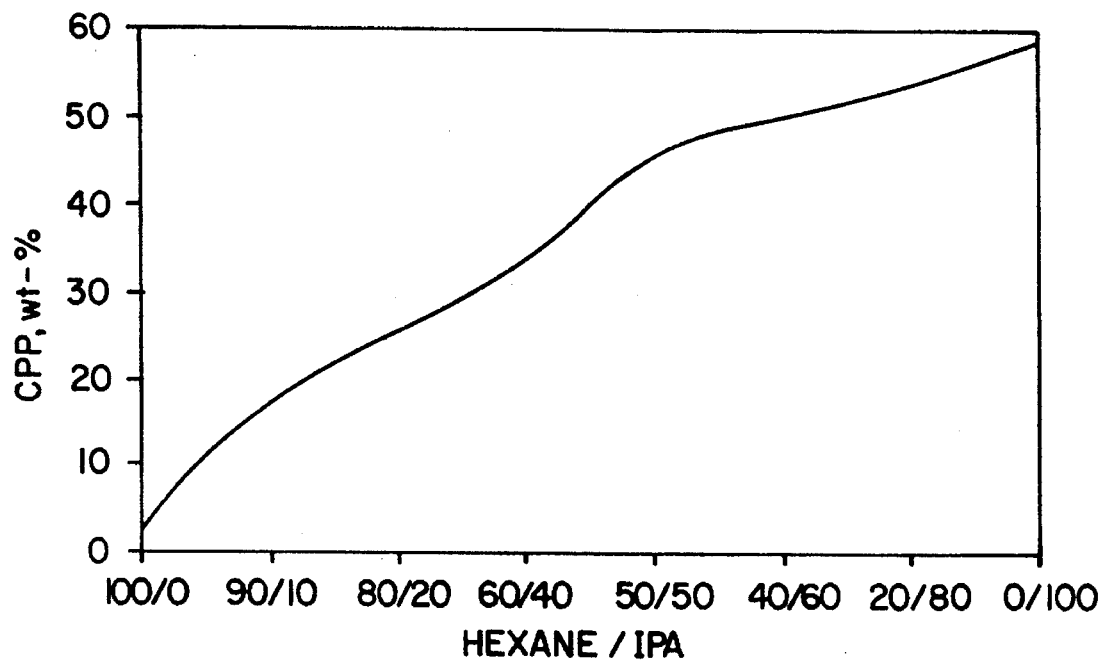
FIG. 6 shows solubility properties of racemic 3-chloro-1-phenyl-1-propanol.

Solubility properties of CPP: The solubility of CPP increases substantially as the isopropyl alcohol content increases (FIG. 6).

Mobile phase selection: A mixture of hexane and isopropyl alcohol is a suitable mobile phase.

Figure 7:
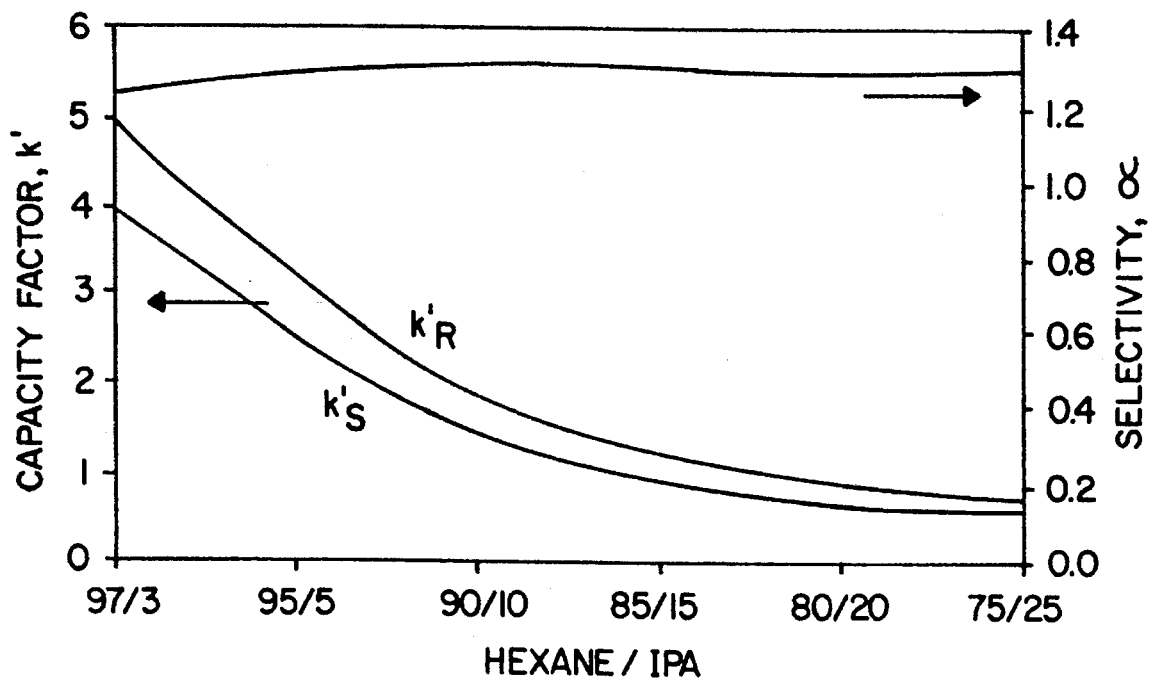
FIG. 7 shows the effect of mobile phase composition on separation of racemic 3-chloro-1-phenyl-1-propanol.

Effect of mobile phase composition: When the isopropyl alcohol content is increased, the capacity factors are reduced (FIG. 7). The selectivity remains constant.

Figure 8:
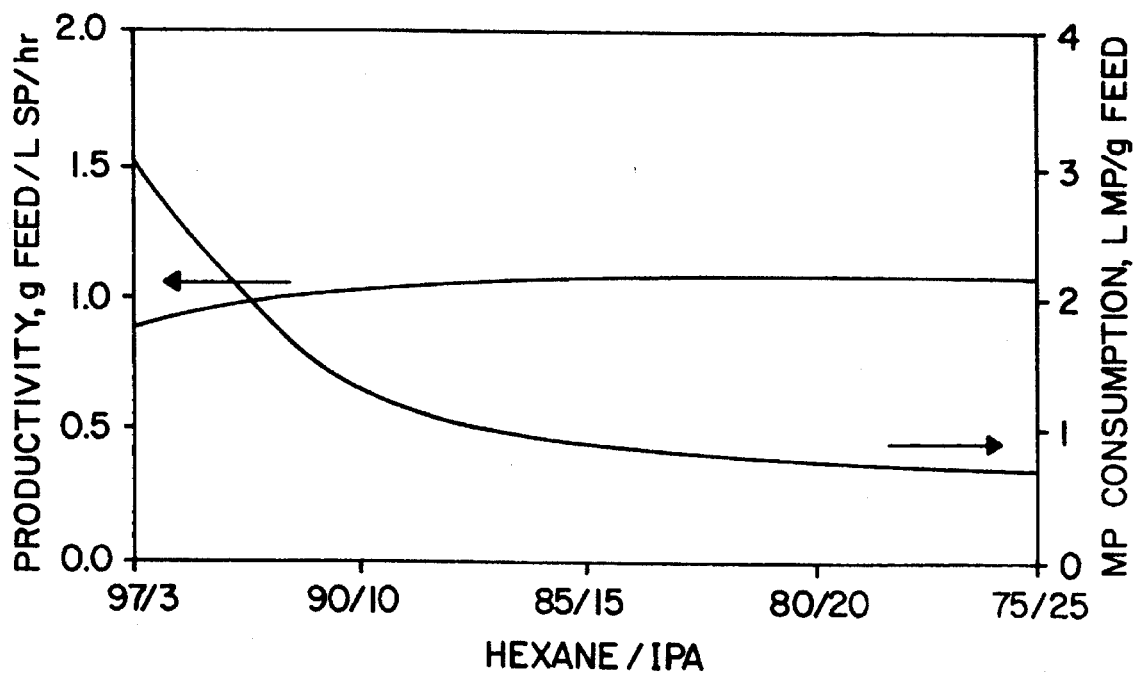
FIG. 8 depicts the productivity and mobile phase consumption for resolution of racemic 3-chloro-1-phenyl-1-propanol.

Selection of mobile phase composition. Productivity and solvent consumption were determined by assuming the maximum solubility of CPP at each mobile phase composition (FIG. 8). The productivity increases from 0.9 to 1.1 g feed/L stationary phase/hr as the isopropyl alcohol content of the mobile phase increases. Even though the solubility of CPP is high, the productivity is low because the selectivity is low. The mobile phase consumption decreases as the isopropyl alcohol content of the mobile phase increases. The optimal mobile phase composition is a mixture of 75% hexane and 25% isopropyl alcohol when productivity is the highest and mobile phase consumption is lowest. At these conditions, the capacity factors are less than 1.

With the optimal mobile phase composition of 75% hexane and 25% isopropyl alcohol, a total cost savings of about 22% is realized relative to a mobile phase mixture of 97% hexane and 3% isopropyl alcohol The cost of the stationary phase is a major component of the cost savings.

Conclusions: The optimal mobile phase composition is a blend of 75% hexane and 25% isopropyl alcohol. The low selectivity of the separation leads to high stationary phase costs when the mobile phase is 75% hexane and 25% isopropyl alcohol. Methods to increase the life of the stationary phase would make the separation of CPP more cost-effective.

Separation of Propranolol

Propranolol, a beta blocker, is currently sold as a racemic mixture. The beta-blocking properties are found in the levorotary enantiomer, (S)-propranolol.

Stationary phase selection: CHIRALCEL OD shows good selectivity for the separation of propranolol enantiomers.

Solubility Properties of propranolol: The solubility of propranolol increases from 2 weight percent in an 80-20 mixture of hexane and isopropyl alcohol to about 6 weight percent for a 30- 70 blend.

Mobile phase selection: Hexane modified with isopropyl alcohol is a suitable mobile phase.

Figure 9:
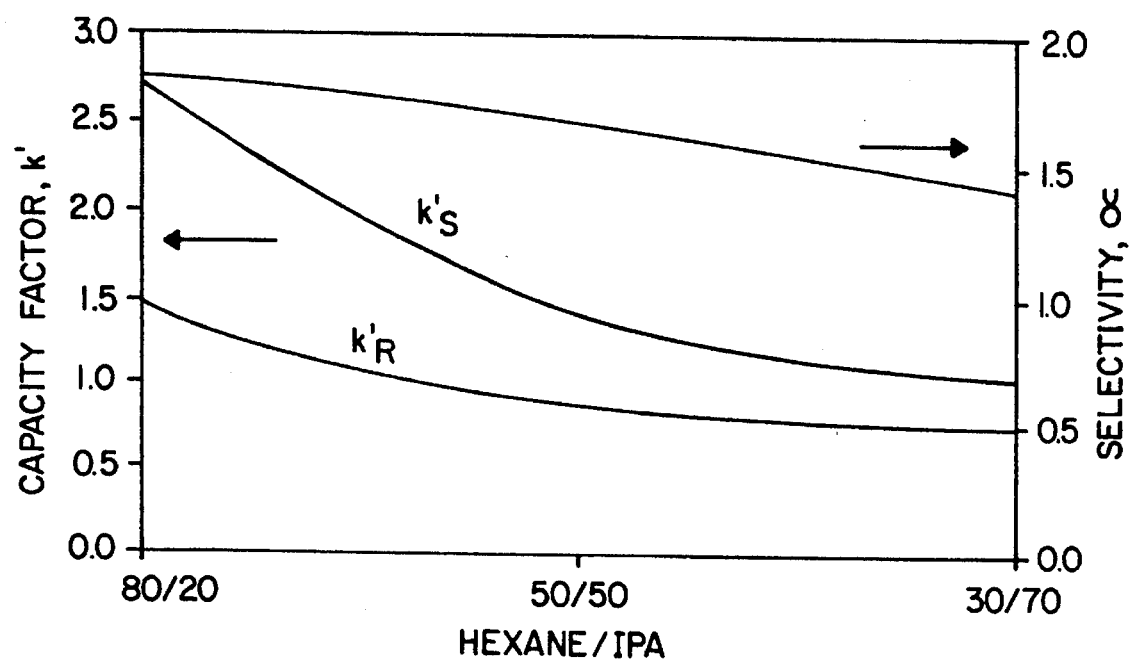
FIG. 9 portrays the effect of mobile phase composition on racemic propanolol separation.

Effect of mobile phase composition: When the isopropyl alcohol content is increased, the capacity factors are reduced (FIG. 9). The selectivity decreases as the isopropyl alcohol content increases.

Figure 10:
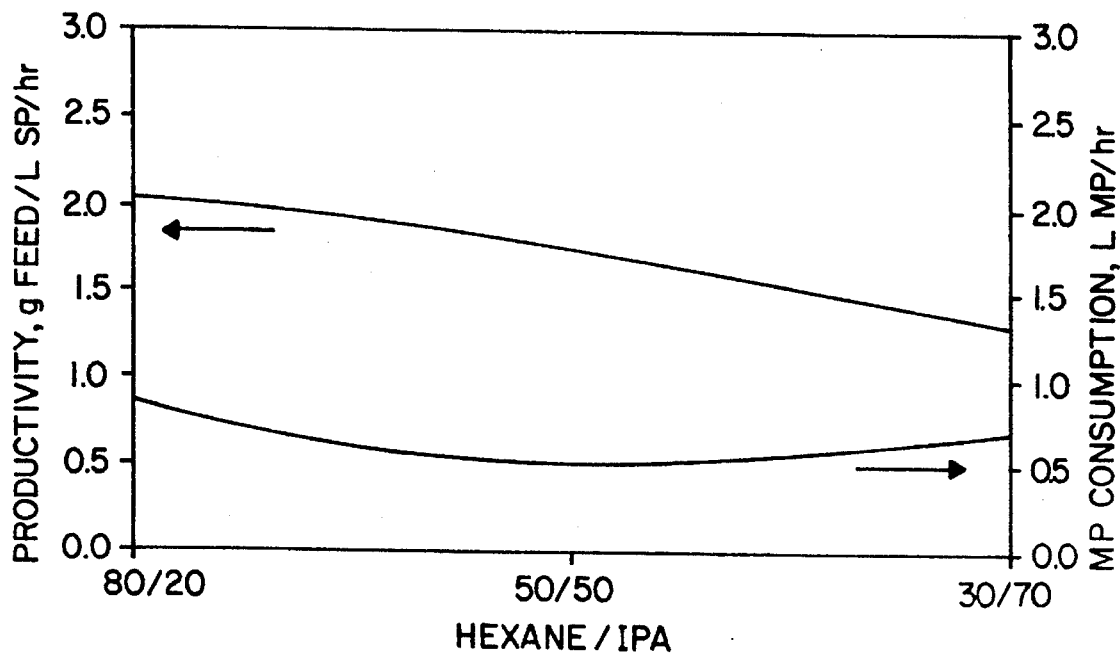
FIG. 10 shows the productivity and mobile phase consumption for racemic propanolol resolution.

Selection of mobile phase composition: Productivity and mobile phase consumption were determined by assuming the maximum solubility of propranolol at each mobile phase composition (FIG. 10). The productivity decreases from 2.0 to 1.3 g feed/L stationary phase/hr as the isopropyl alcohol content of the mobile phase increases. The mobile phase consumption is relatively low, ranging from 05 to 0.8 L mobile phase/g feed.

To determine the optimum mobile phase composition, the cost associated with higher stationary phase requirements must be compared to the savings achieved with lower mobile phase consumption. The cost of the stationary phase plays a major role in determining the optimal operating conditions.

Figure 11:
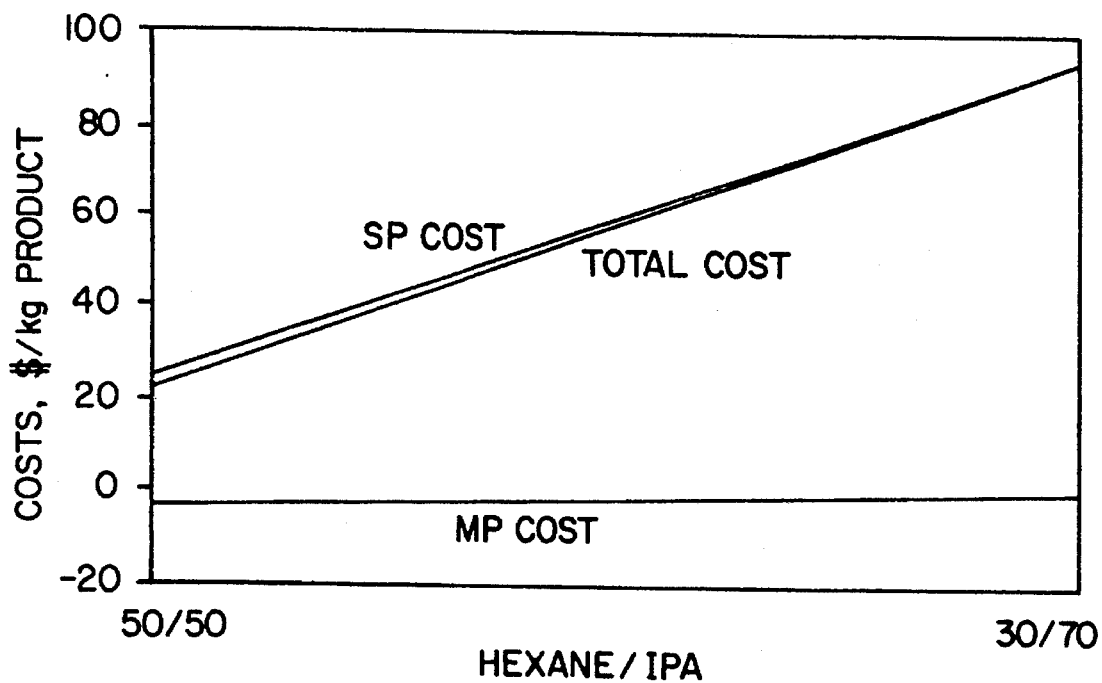
FIGS. 11 and 12 show some hypothetical costs.
Figure 12:
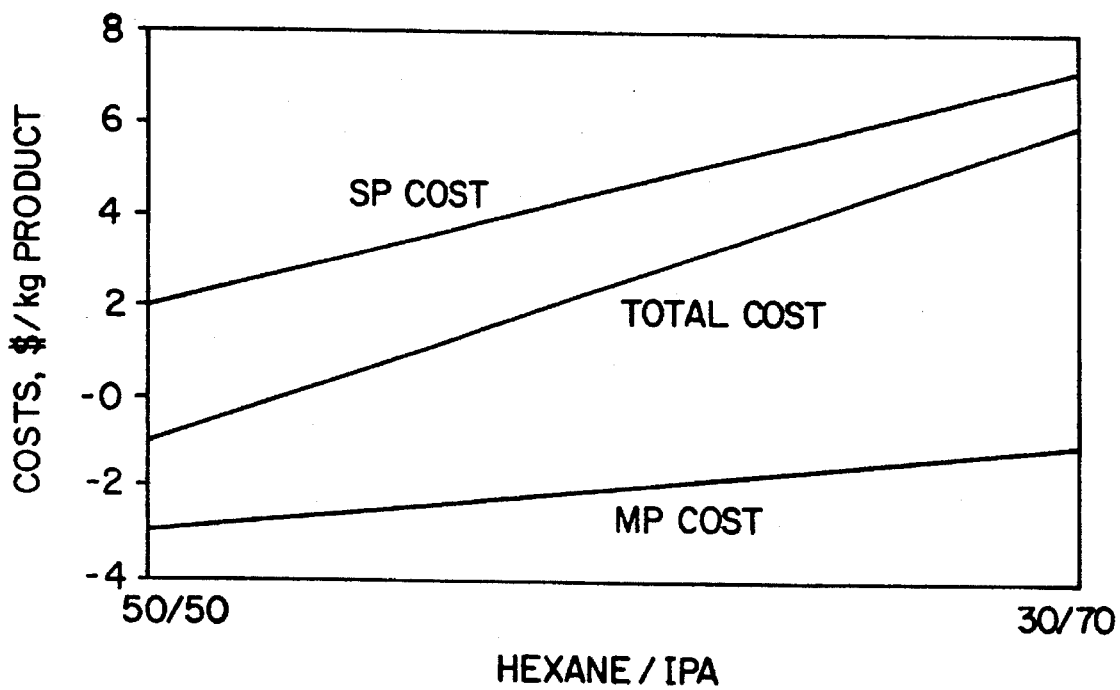

With a stationary phase cost of $4,000/kg, the optimal mobile phase composition is an 80-20 mixture of hexane and isopropyl alcohol (FIG. 11). The cost associated with the increased stationary phase requirement is significantly higher than the savings achieved with a lower Mp consumption. Operating with a 50/50 blend of hexane and isopropyl alcohol is slightly more attractive when the stationary phase cost is $300/kg (FIG. 12). With a low stationary phase cost, the savings associated with solvent recovery become significant.

Conclusions: The optimal operating conditions for propranolol are strongly dependent on the stationary phase cost. The savings associated with reduced solvent consumption are realized when the stationary phase costs are low.

General Guidelines

The solubility of the feed material in the mobile phase is an important criterion for achieving a cost-effective separation using SMB technology. Productivity will be low if the feed has low solubility in the mobile phase of choice and the selectivity of the separation is low. Low productivity leads to high stationary phase requirements.

With high stationary phase costs, the savings in solvent recovery costs are less significant. A cost-effective SMB separation requires that the selectivity of the separation and the life of the stationary phase be maximized. With low stationary phase costs, the solvent recovery costs become significant. In most cases, it is desirable to operate with an mobile phase composition that gives capacity factors less than 1.

From the foregoing, distinctions between SMB and traditional elution chromatography, whether analytical or preparative batch chromatography, are apparent. In preparative chromatography, high resolution is required to obtain high purity and recovery. Resolution is proportional to $k'$ and the use of low $k''$s can result in low resolution. With SMB operation, however, good resolution (greater than 1) is not required. The countercurrent mode of operation is inherently more efficient and high purity and recovery can be achieved by "peak shaving." From the perspective of the elution chromatographer, the use of low values of $k'$ in SMB operation is unexpected. Successful chiral separations via SMB can be routinely achieved working at a resolution less than 1, contrary to the current guidelines for elution chromatography. See, e.g., Kirkland and Snyder, page 52, who teach that the optimum $k'$ range in elution chromatography is between 1 and 10.

Specifically, for cases where $k'<1$ the chromatographic resolution, Rs, is necessarily less than 0.5. But at these conditions for separation of a 1:1 mixture of 2 components (which is necessarily the case in resolution of a racemic mixture!) the cutoff at the midpoint of the eluted peak affords 84% purity with about 84% recovery; see p. 34, FIG. 2.11 and page 48, FIG. 2.21, of Kirkland and Snyder, op. cit. However, working with SMB at an Rs of 0.5 one can readily obtain a purity of 95% at a recovery of 95%, which dramatically demonstrates the unexpected difference between elution chromatography and the SMB process. Separating enantiomers with a purity of at least 98% and a recovery of at least 98% is a more preferred mode of operation which is generally readily achievable according to the practice of our invention.

What is claimed is:

1. In a process for the separation of at least one enantiomer from a mixture of chiral organic materials by simulated moving bed chromatography using an achiral liquid mobile phase and a solid stationary phase having at least one organic material with a chiral recognition site, the improvement comprising effecting said separation using an achiral liquid mobile phase which affords a retention capacity, $k'$, such that $0.1<k'<1.0$.

2. The process of claim 1 where the separation affords at least one of the enantiomers in at least 95% purity with at least 95% recovery.

3. The process of claim 1 where the separation affords at least one of the enantiomers in at least 98% purity with at least 98% recovery.

\* \* \* \* \*

(12) EX PARTE REEXAMINATION CERTIFICATE (6680th)
United States Patent
Priegnitz et al.

(10) Number: US 5,518,625 C1
(45) Certificate Issued: Mar. 3, 2009

(54) CHIRAL SEPARATIONS BY SIMULATED MOVING BED CHROMATOGRAPHY OPERATING AT LOW K' VALUES

(75) Inventors: James W. Priegnitz, Elgin, IL (US); Beth McCulloch, Clarendon Hills, IL (US)

(73) Assignee: UOP, Des Plaines, IL (US)

Reexamination Request:
No. 90/006,706, Jul. 11, 2003

Reexamination Certificate for:
Patent No.: 5,518,625
Issued: May 21, 1996
Appl. No.: 08/387,984
Filed: Feb. 13, 1995

(51) Int. Cl.
*B01D 15/08* (2006.01)

(52) U.S. Cl. .............. 210/659; 210/198.2; 210/656; 435/280

(58) Field of Classification Search .......... 210/198.2, 210/635, 656, 659; 435/280
See application file for complete search history.

(56) References Cited

U.S. PATENT DOCUMENTS 5,256,293 A * 10/1993 Pirkle et al. ............... 210/635
5,434,298 A * 7/1995 Negawa et al. ............ 560/248
5,889,186 A * 3/1999 Gattuso .................... 564/304

OTHER PUBLICATIONS

Textbook "Introduction to Modern Liquid Chromatography" Second Edition, L.R. Snyder & J.J. Kirkland, Copyright 1979, Chapter 6 (pp. 246–268).*

Ching, C.B., et al., "Preparative resolution of praziquantel enatiomers by simulated counter–current chromatography", *Journal of Chromatography*, 634 (1993) pp. 215–219, published on Mar. 6, 1993.

* cited by examiner

*Primary Examiner*—Joseph W Drodge

(57) ABSTRACT

Resolution of a racemic mixture of organic materials by simulated moving bed chromatography using a chiral stationary phase can be routinely effected at atypically low values of k' with recoveries of at least 95% and an optical purity of at least 95%. In particular, values in the range $0.1 < k' < 1.0$ are recommended with a resulting savings in mobile phase consumption, inventory, and recovery.

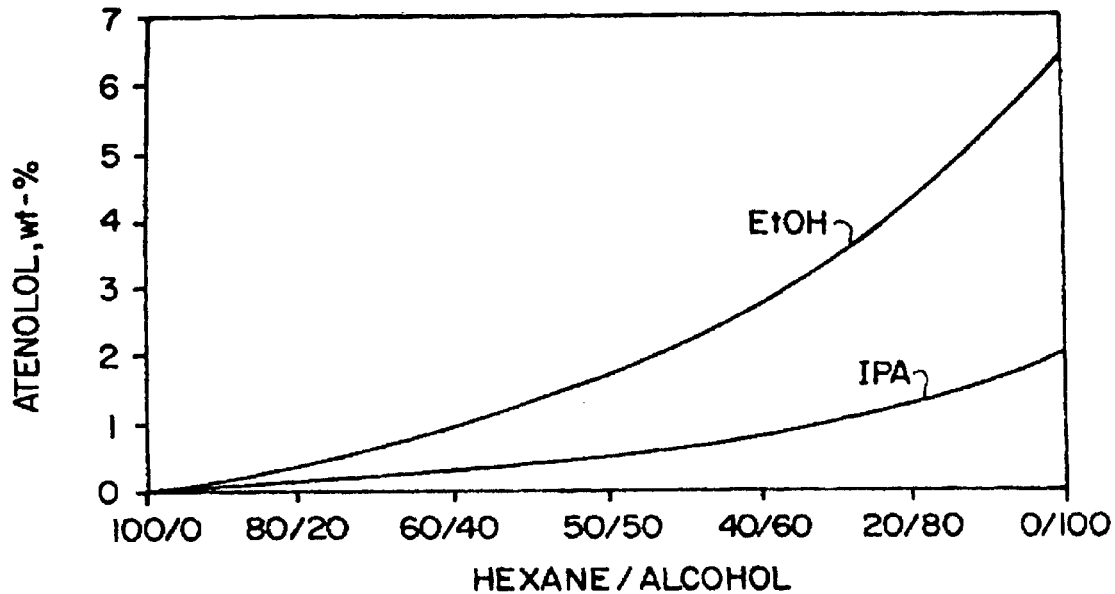

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–3 are cancelled.

* * * * *